(12) United States Patent
Ciani

(10) Patent No.: US 6,927,409 B2
(45) Date of Patent: Aug. 9, 2005

(54) METHOD TO DETECT DEFECTS IN THE SHAPE OF A ROLLED PRODUCT AND RELATIVE DEVICE

(75) Inventor: Lorenzo Ciani, Udine (IT)

(73) Assignee: Danieli Automation SpA, Buttrio (IT)

( * ) Notice: Subject to any disclaimer, the term of this patent is extended or adjusted under 35 U.S.C. 154(b) by 228 days.

(21) Appl. No.: 10/347,980

(22) Filed: Jan. 21, 2003

(65) Prior Publication Data
US 2003/0136925 A1 Jul. 24, 2003

(30) Foreign Application Priority Data
Jan. 21, 2002 (IT) .................................... UD2002A0009

(51) Int. Cl.$^7$ .............................................. G01B 11/04
(52) U.S. Cl. .................................. 250/559.45; 356/383
(58) Field of Search ...................... 250/559.12, 559.13, 250/559.14, 559.15, 559.45; 73/570

(56) References Cited

U.S. PATENT DOCUMENTS

| | | | |
|---|---|---|---|
| 4,880,991 A | 11/1989 | Boehnlein et al. | |
| 5,094,600 A | 3/1992 | Sikora | |
| 5,383,021 A | * 1/1995 | Hanna | ........................ 356/634 |
| 5,930,734 A | 7/1999 | Hofmann et al. | |

FOREIGN PATENT DOCUMENTS

| | | |
|---|---|---|
| DE | 34 10 149 A1 | 10/1985 |
| EP | 1 154 226 A2 | 11/2001 |
| FR | 2 636 731 A1 | 3/1990 |
| GB | 1 143243 | 2/1969 |
| GB | 2 149 101 A | 6/1985 |

* cited by examiner

*Primary Examiner*—David Porta
*Assistant Examiner*—Tony Ko
(74) *Attorney, Agent, or Firm*—Akin Gump Strauss Hauer & Feld, LLP

(57) ABSTRACT

Method and device to detect defects (11a, 11b, 11c) in the section shape of a product (10), wherein the following steps are provided:

a step of constructing and memorizing a plurality of families of functions each of which describes a correlated type of defect (11a, 11b, 11c), or combination of defects which can be found in a product (10) observed in relation to the processing performed on the product (10);

a step of dimensional measuring of the shadow cast by the product (10) when it is illuminated by a beam of light;

a step of constructing a graphical representation relating to the development of the dimension of the shadow for a specific dimensional sector of the product (10); and a step of comparing the graphical representation of the functions memorized to identify the function which most resembles the representation obtained by the detection in order to classify the type, and to determine the entity, of the defect (11a, 11b, 11c) present in the section of the product (10).

10 Claims, 4 Drawing Sheets

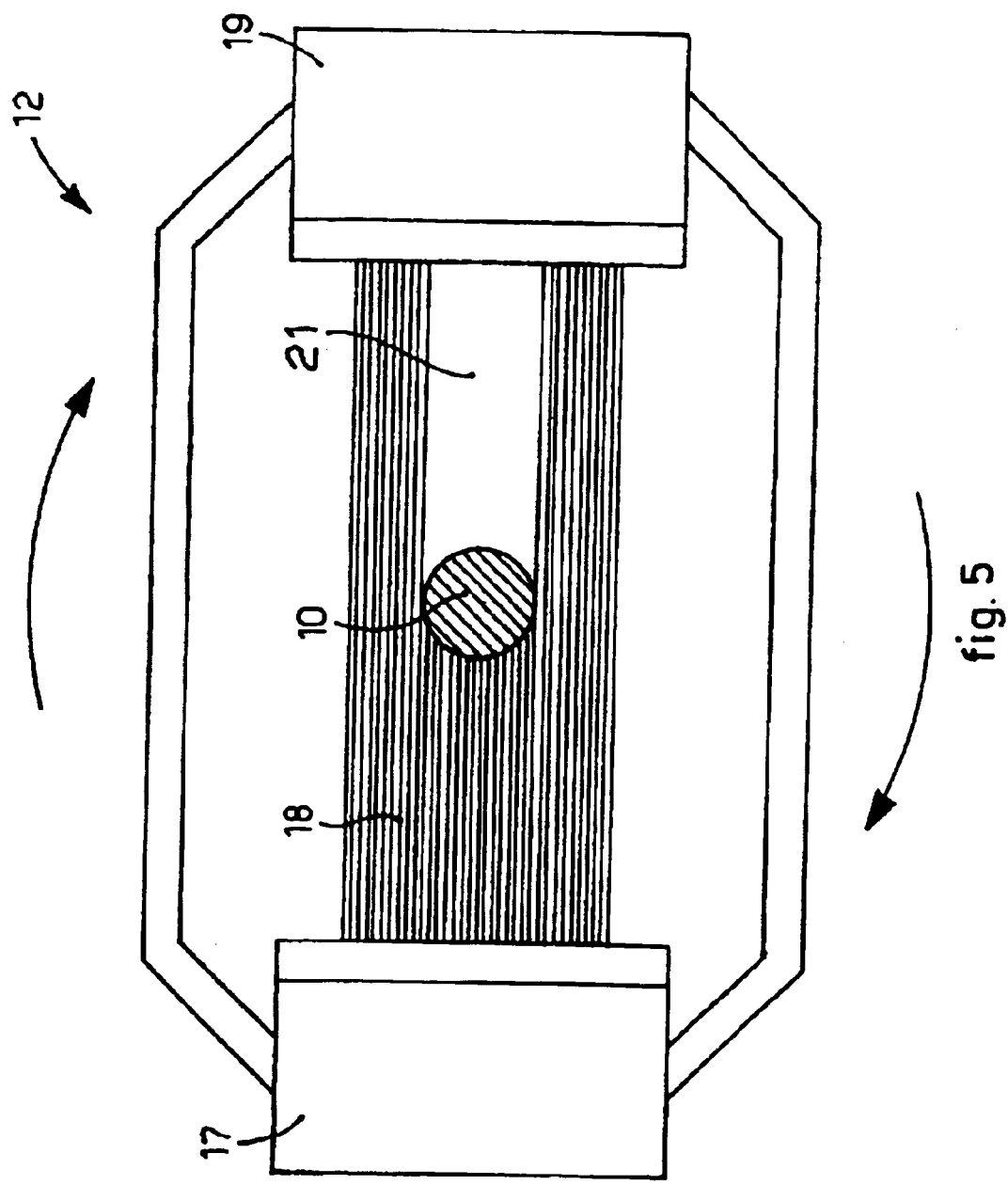

METHOD TO DETECT DEFECTS IN THE SHAPE OF A ROLLED PRODUCT AND RELATIVE DEVICE

BACKGROUND OF THE INVENTION

The invention concerns a method to inline detect defects in the section shape of a rolled product.

The invention also concerns a relative device able to detect said defects in shape.

In the following description, rolled product should also be taken to mean a product emerging from similar or comparable processing, such as drawing or extrusion.

Moreover, even if the invention is applied preferentially to products with a round nominal section, or comparable thereto, it can also be applied to products of different section, such as polygonal, star-shaped, three-lobed or other.

The invention is applied advantageously, though not exclusively, in the steel-making industry to obtain an automatic inline detection of the defects in section shape of a bar or wire emerging from at least a rolling, drawing or extrusion step. To be more exact, the invention is applied preferentially in a production line of a plant for the hot rolling of long products.

The state of the art includes various systems and methods to inline detect defects in shape and/or surface defects on bars or wire during or at the end of rolling, drawing or extrusion operations. For example, electromagnetic devices are known which, by means of coils emitting an electromagnetic field and relative reception coils, detect the presence of surface defects, such as cracks or micro-fissures, in metal bars or wire being worked along a rolling line.

To detect defects in shape, the state of the art uses rotary optical sensors, suitable to rotate around the rolled product being worked and to determine the presence of oval shapes, localized buckling, or other type of deformation or defect.

The use of such rotary optical sensors, however, has proved to be not completely efficient because, due to the rotation on its own axis to which the product is subjected as it advances, the rotary sensors are often able to detect only the entity but not the type of defect in the section shape, which cannot be distinguished with precision.

This inability to distinguish the type of defect does not allow to identify the causes of said defects, for example an incorrect alignment of the rolling rolls, their closure above or below the nominal design value, or wear or damage to the rolling, drawing or extrusion equipment, and therefore it does not allow to make the corrections necessary to restore more suitable working conditions.

Moreover, in order to eliminate this shortcoming, the state of the art has recourse to complex equipment which, using several detectors from different points and triangulation techniques, allow to deduce the type of defect found too. However, such equipment is very expensive and onerous with regard to the plant, so that it is often uneconomical and cannot be used on all plants.

The present Applicant has devised and embodied this invention to overcome the shortcomings of the state of the art and to obtain further advantages.

BRIEF SUMMARY OF THE INVENTION

The invention is set forth and characterized in the respective main claims, while the dependent claims describe other innovative characteristics of the main embodiment.

The purpose of the invention is to allow to distinguish the type, and to determine the entity, of defects in section shape of a product being worked, particularly a rolled metal product, using a relatively simple device which does not require expensive equipment and complex processing and calculation methods, and can be installed substantially in every type of plant.

In accordance with this purpose, the device according to the invention comprises means to measure the dimension of the shadow cast by the product analyzed when it is illuminated by at least a beam of light, means to achieve a graphical representation of the development of the dimension in relation to at least a specific dimensional sector of the product, and means able to compare the graphical representation with a plurality of graphical representations, each characteristic of a specific defect in shape of the product, in order to distinguish the defect or the combination of defects found, identifying the most similar graphical representation to that detected.

In other words, the device according to the invention is suitable to provide an index of similarity between a graphical representation detected according to a specific measurement of a shadow made on the product, and a plurality of reference graphical representations constructed according to a knowledge of the defects in shape which are typical of the product as can be found depending on the type of plant and the type of processing considered.

Each of the graphical representations is characteristic of a typical defect, both relating to the type and to the entity, or of a typical combination deriving when two or more defects which can occur simultaneously on the product are superimposed.

In a preferential embodiment, the graphical representation of the development of the shadow which is used consists of the polar diagram which identifies the development of the diameter of the product with the variation of the angle at the center considered.

According to this preferential embodiment, the means to measure the dimension of the shadow comprise a measurer able to perform a rotation around its own axis, in order to construct the polar development of the dimension of the shadow on at least one specific angular sector of the product considered.

According to a variant, each detection comprises at least an inspection made on at least two sectors, opposite and symmetrical with respect to the center of the product, so as to allow to distinguish the type of defect, or the combination of defects, by means of a rotation of the measurer limited to a reduced angle of the product being observed.

The method according to the invention therefore provides a preliminary step of constructing and memorizing a plurality of function families, each one able to describe a correlated plurality of possible types of defects, or combinations of defects, which can be found in a specific angular sector of the product observed in relation to the processing performed on the product. Then, the dimension of the shadow on the product being worked is measured and the relative polar diagram is constructed; according to a variant, the polar diagram is suitably filtered and pre-processed, for example normalized, so that it is not influenced by the variability of the dimension of the product observed.

The polar diagram and the pre-memorized functions are then compared, in order to identify the one most similar to the diagram obtained with the detection. Depending on this identification of the most similar function, the method allows to classify the type of defect on the section of the product, and also to determine the entity thereof; the greater the number of functions for every family of defects considered, the greater the degree of approximation.

According to a variant, the invention also provides a step of inverse processing of the result obtained, for example an anti-normalization.

BRIEF DESCRIPTION OF THE SEVERAL VIEWS OF THE DRAWINGS

The foregoing summary, as well as the following detailed description of perferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 5 is a functional diagram of a preferred embodiment of a measurement assembly.

DETAILED DESCRIPTION OF THE INVENTION

Figure 1A:
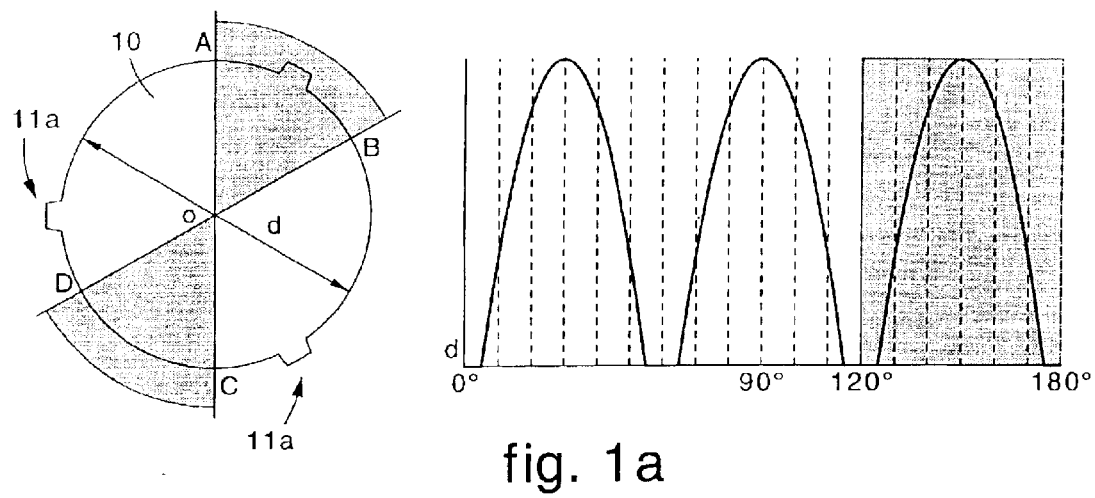
FIGS. 1a, 1b and 1c show three possible cases of defects in the section shape with the relative polar diagram of the development of the diameter as the angle at the center varies.
Figure 1B:
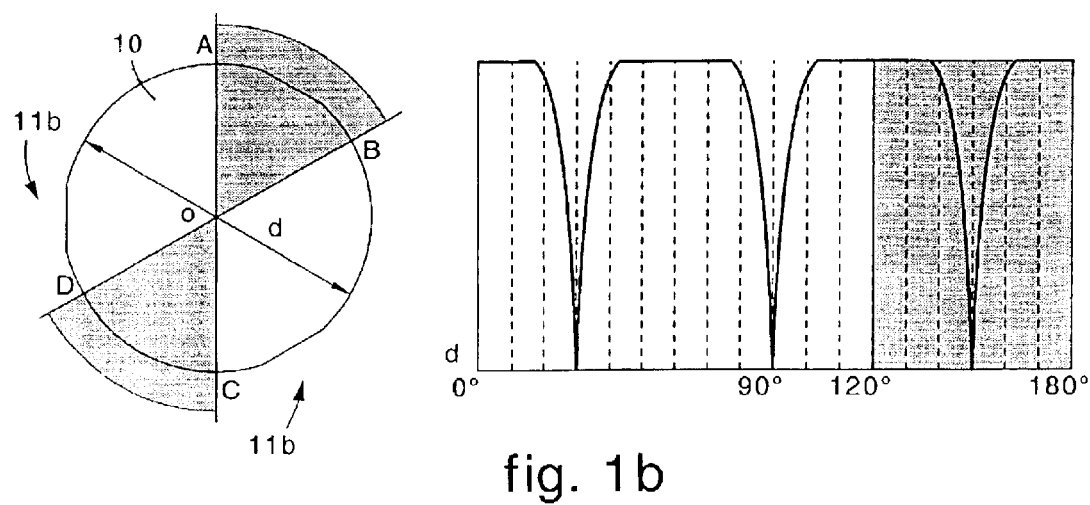
Figure 1C:
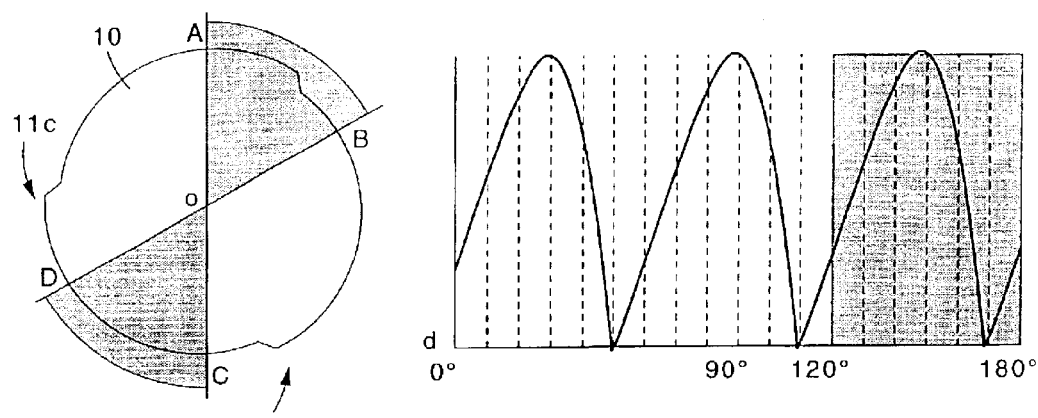

With reference to the attached drawings, FIGS. 1a, 1b and 1c show examples of three typical cases of defects in the section shape of a rolled product 10 which can be found in a rolling mill with 3-high stands having the rolls located at 120° with respect to each other (Kocks® stand).

Given the arrangement of the rolling rolls, the defects (indicated for the three cases respectively by 11a, 11b and 11c) due to imprecise alignment, incorrect closure or wear or imperfections of the rolls are repeated symmetrically on the circumference of the product 10. Such typical defects refer respectively to a case of overfill (FIG. 1a), underfill (FIG. 1b) and a case of mistaken centering (shift) (FIG. 1c).

The device 20 according to the invention comprises at least an assembly 17 able to emit a beam of light 18 focused at infinity towards the product 10 and an assembly 19, of a substantially conventional type and therefore not shown in detail here, able to measure the shadow 21 cast by the product 10 when it is hit by said beam of light 18.

Figure 4:
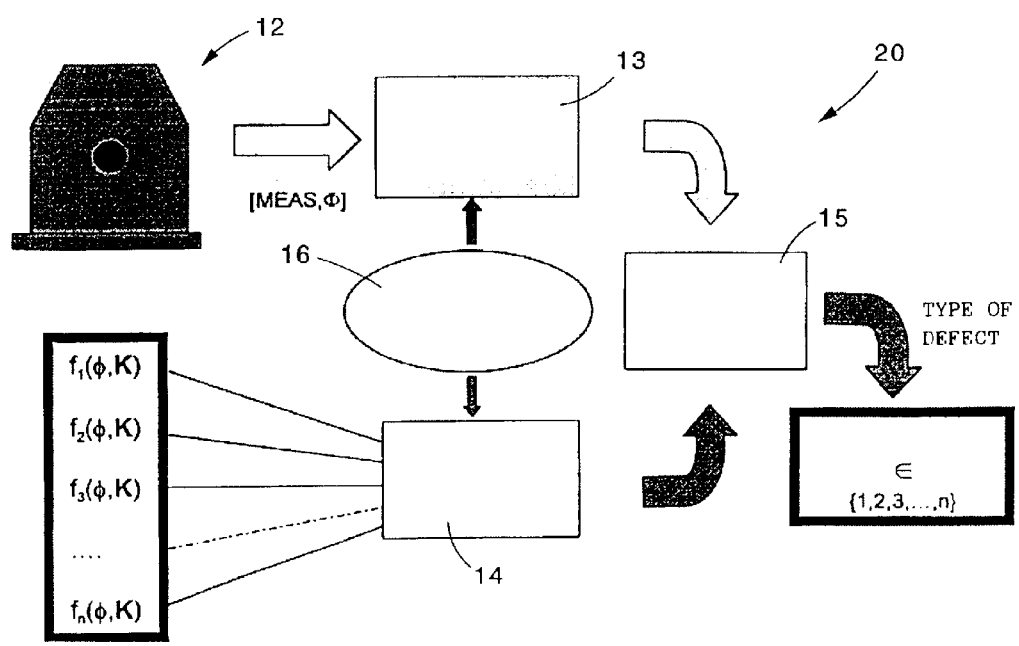
FIG. 4 shows a flow chart of the device according to the invention.

A measurement assembly 12 to measure the shadow 21, identified is the device 20 shown schematically in FIG. 4 by the reference number 12, is suitable to perform a rotation for a certain angle around its own axis in order to allow processing and calculation means 13, associated with the measurement assembly 12, to construct the polar diagram of the dimension of the shadow as the angle at the center considered varies. To be more exact, in this case, the polar diagram represents the variable development of the diameter "d" of the product 10 according to the angular position of the measurer.

As shown in FIGS. 1a–1c, in this specific case the inspection can be limited to two angular sectors, indicated respectively by AB and CD, symmetrical with respect to the nominal center O of the product 10 and defining an angle at the center of about 60° in fact, given the type of rolling plant considered, it is certain that in at least one of said sectors there will be the defect 11a, 11b or 11c to be detected.

Clearly, as the type of plant changes, as well as the type and shape of the product 10 to be analyzed, then also the parameters of use and management of the measuring device according to the invention will vary.

As can be seen in the attached FIGS. 1a–1c, each typical defect 11a–11c is defined by a specific polar diagram with a peculiar and characteristic development of the relative curve.

Also when combinations of two or more defects are to be found simultaneously in the rolled product 10 being worked, the relative polar diagrams will be characterized by a peculiar and characteristic development.

Figure 2:
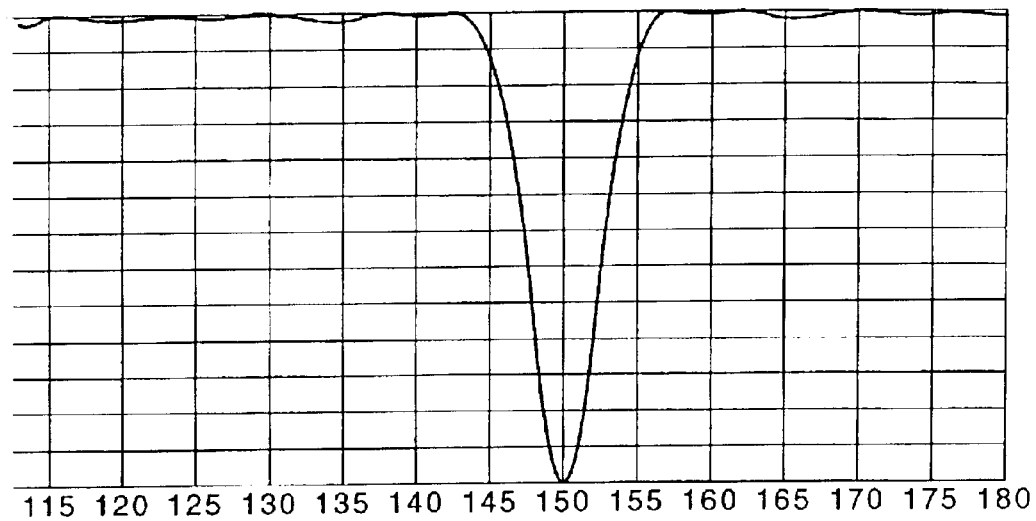
FIG. 2 shows the polar diagram relating to the case of FIG. 1b, limited to the angular sector where there is the defect.

If we limit the inspection to a reduced sector of the section, in this case 120 to 180°, and take the defect shown in FIG. 1b (underfill) as an example, the processing and calculation means 13 are able to construct and represent the typical and univocal polar diagram for the type of defect found in the angular sector considered (FIG. 2).

The graphical representation is made after the data arriving from the shadow measurement assembly 12 have been suitably filtered and pre-processed by said processing and calculation means 13, for example normalized, in order to reduce the influence of the section shape and the dimension of the product 10 on the measurement.

The present invention provides a preliminary step of constructing, by a function generator 14, a plurality of function families, identified in FIG. 4 by fi ($\phi$, K), . . . , fn ($\phi$, K), each of said families being able to describe and classify "n" possible types of defects or combinations of defects in the section shape of the product 10 in the angular sector $\phi 0 - \phi 1$ considered.

K represents generally a vector of parameters which identifies a specific function inside the relative family, in relation to the different and variable entity of the defect of the specific type, considered.

Figure 3:
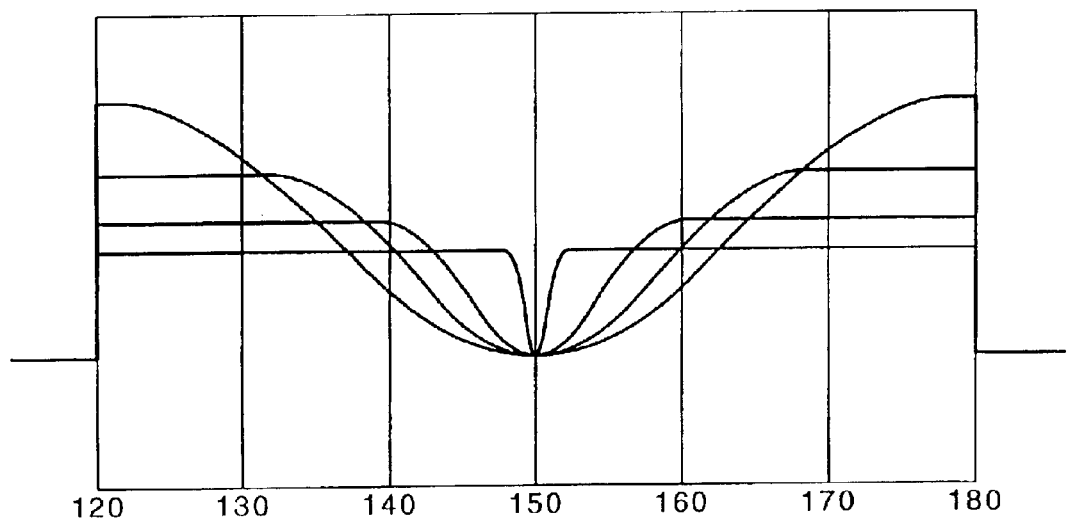
FIG. 3 shows a family of curves used as functions of comparison in order to recognize the defect in shape relating to the case shown in FIG. 1b.

In the case considered here of the underfill defect as in FIG. 1b, FIG. 3 shows the family of normalized curves (functions) which describe this type of defect as its entity varies.

The normalized polar diagram constructed by the processing and calculation means 13 based on the measurement of the shadow is then compared, in a suitable correlation assembly 15, with the function families constructed by the generator 14.

A parameterization step may be provided, performed by a suitable calculation unit 16, to make the diagrams constructed according to the measurement compatible and comparable with the standardized and pre-memorized functions.

The correlation assembly 15 is suitable to identify the degree of maximum correlation between the curves which is obtained in the case of maximum similarity between the data arriving from the measurement assembly 12 and one of the input functions produced by the generator 14. According to the family to which the function with the maximum degree of similarity belongs, the device 20 allows to classify, during the production process, the type of defect found among the "n" defects classified.

Moreover, if the function with maximum similarity belongs to a family which describes a combination of two or more defects, the correlation assembly 15 is suitable to perform several sequential cycles of comparison in order to distinguish the relative incidence of the two or more types of defects present, in order to determine the entity of each individual defect found.

An inverse processing of anti-normalization can also be performed on the results obtained.

Thanks to the fact that the type and entity of the defects present in the product are identified, the device 20 therefore allows to perform correction operations to restore the most suitable working conditions.

It is clear however that modifications and/or additions of parts can be made to the method and device to detect defects in shape as described heretofore without departing from the field and scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method to detect defects (11a, 11b, 11c) in the section shape of a product (10), characterized in that it provides:
    a step of constructing and memorizing a plurality of families of functions, each family being able to describe a correlated type of defect (11a, 11b, 11c), or combination of defects, which can be found in a product (10) observed in relation to the processing performed on said product (10);
    a step of dimensional measuring of the shadow cast by said product (10) when it is illuminated by at least a beam of light;
    a step of constructing a graphical representation relating to the development of said dimension of the shadow for at least a specific dimensional sector of said product (10); and
    a step of comparing said graphical representation and said functions memorized to identify the function which most resembles the representation obtained by the detection in order to classify the type, and to determine the entity, of the defect (11a, 11b, 11c) present in the section of said product (10), wherein said graphical representation is the polar diagram of the development of the nominal diameter ("d") of said product (10) as the angle at the center varies.

2. The method as in claim 1, characterized in that it provides at least a step of normalization of the data obtained from the dimensional measurement of the shadow before comparison with said memorized functions.

3. The method as in claim 1, characterized in that said step of dimensional measurement of the shadow is performed by means of inspecting at least one angular sector of said product (10).

4. The method as claim 1, characterized in that said step of dimensional measuring of the shadow is performed by means of inspecting at least two opposite and symmetrical sectors with respect to the center (O) of said product (10).

5. A method to detect defects (11a, 11b, 11c) in the section shape of a product (10), characterized in that it provides:
    a step of constructing and memorizing a plurality of families of functions, each family being able to describe a correlated type of defect (11a, 11b, 11c), or combination of defects, which can be found in a product (10) observed in relation to the processing performed on said product (10);
    a step of dimensional measuring of the shadow cast by said product (10) when it is illuminated by at least a beam of light;
    a step of constructing a graphical representation relating to the development of said dimension of the shadow for at least a specific dimensional sector of said product (10); and
    a step of comparing said graphical representation and said functions memorized to identify the function which most resembles the representation obtained by the detection in order to classify the type, and to determine the entity, of the defect (11a, 11b, 11c) present in the section of said product (10), wherein after the type of combination of defects has been identified, the method provides a sequential cycle of comparisons to obtain information on the entity of the individual defects (11a, 11b, 11c) found in said product (10).

6. A device to detect defects (11a, 11b, 11c) in the section shape of a product (10), characterized in that it comprises measuring means (12) able to measure a dimension of a shadow cast by a product (10) analyzed when it is illuminated by at least a beam of light, means (13) able to make a graphical representation in the form of a polar diagram of the development of said dimension in relation to at least a specific dimensional sector of said product (10), and means (15) able to compare said graphical representation with a plurality of graphical representations, each one characteristic of a specific defect (11a, 11b, 11c), or a combination of defects, in the section shape of the product (10), in order to distinguish the defect found by identifying the graphical representation most similar to that detected.

7. The device as in claim 6, characterized in that said graphical representations characteristic of a specific defect (11a, 11b, 11c) are obtained by function generating means (14) able to construct and memorize a plurality of functions f1($\phi$, K), ($\phi$, K), each one able to describe and classify a possible defect or combination of defects, both according to type and according to entity, in the section shape of a specific dimensional sector of said product (10).

8. A device to detect defects (11a, 11b, 11c) in the section shape of a product (10), characterized in that it comprises measuring means (12) able to measure the dimension of the shadow cast by the product (10) analyzed when it is illuminated by at least a beam of light, means (13) able to make a graphical representation of the development of said dimension in relation to at least a specific dimensional sector of said product (10), and means (15) able to compare said graphical representation with a plurality of graphical representations, each one characteristic of a specific defect (11a, 11b, 11c), or a combination of defects, in the section shape of the product (10), in order to distinguish the defect found by identifying the graphical representation most similar to that detected wherein, said measuring means (12) able to measure the dimension of the shadow comprise at least an emitter of a beam of light focused at infinity and a measurer able to perform an angular rotation around its own axis.

9. The device as in claim 6, characterized in that it comprises processing and calculation means (13) associated with said measuring means (12) and able to perform a processing and at least a normalization of the data supplied by said measuring assembly (12).

10. The device as in claim 6, characterized in that it comprises a calculation unit (16) able to perform a parameterization of data in order to make the diagram made according to the measurement compatible with the pre-memorized functions constructed by said function generator (14).

* * * * *